(12) United States Patent
Patel et al.

(10) Patent No.: US 9,238,605 B2
(45) Date of Patent: Jan. 19, 2016

(54) OXIDATION OF HYDROCARBONS

(71) Applicant: ExxonMobil Chemical Patents Inc., Baytown, TX (US)

(72) Inventors: Bryan A. Patel, Jersey City, NJ (US); Travis A. Reine, Slidell, LA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/421,232

(22) PCT Filed: Sep. 5, 2013

(86) PCT No.: PCT/US2013/058226
§ 371 (c)(1),
(2) Date: Feb. 12, 2015

(87) PCT Pub. No.: WO2014/039653
PCT Pub. Date: Mar. 13, 2014

(65) Prior Publication Data
US 2015/0225326 A1    Aug. 13, 2015

Related U.S. Application Data

(60) Provisional application No. 61/698,169, filed on Sep. 7, 2012.

(51) Int. Cl.
*C07C 45/53*  (2006.01)
*C07C 37/08*  (2006.01)
*C07C 2/66*   (2006.01)
*C07C 407/00* (2006.01)

(52) U.S. Cl.
CPC ............... *C07C 37/08* (2013.01); *C07C 45/53* (2013.01); *C07C 407/00* (2013.01); *C07C 2101/14* (2013.01)

(58) Field of Classification Search
CPC ............ C07C 45/53; C07C 37/08; C07C 2/66
USPC ................................... 568/376, 570, 798, 799
See application file for complete search history.

(56) References Cited

U.S. PATENT DOCUMENTS 2,967,891 A    1/1961    Holder

FOREIGN PATENT DOCUMENTS

| GB | 760367 | 10/1956 |
|----|--------|---------|
| WO | WO 2009/025939 | 2/2009 |
| WO | WO 2009/058527 | 5/2009 |

OTHER PUBLICATIONS

Arends et al., "Selective Catalytic Oxidation of Cyclohexylbenzene to Cyclohexylbenzene-1-hydroperoxide: A Coproduct-free Route to Phenol," Tetrahedron, vol. 58, No. 44, pp. 9055-9061.

*Primary Examiner* — Sikarl Witherspoon
(74) *Attorney, Agent, or Firm* — Siwen Chen; Stephen A. Baehl

(57) ABSTRACT

A process for oxidizing a first hydrocarbon to a corresponding first oxygenate by feeding a first feedstock comprising the first hydrocarbon into an oxidation reactor, contacting the reaction medium with a gas stream comprising $O_2$ in the oxidation reactor, and supplying a hydroperoxide additive to the oxidation reactor. By including the hydroperoxide additive in the reaction medium, foaming at and/or close to the beginning of the oxidation reaction can be significantly reduced.

22 Claims, 1 Drawing Sheet

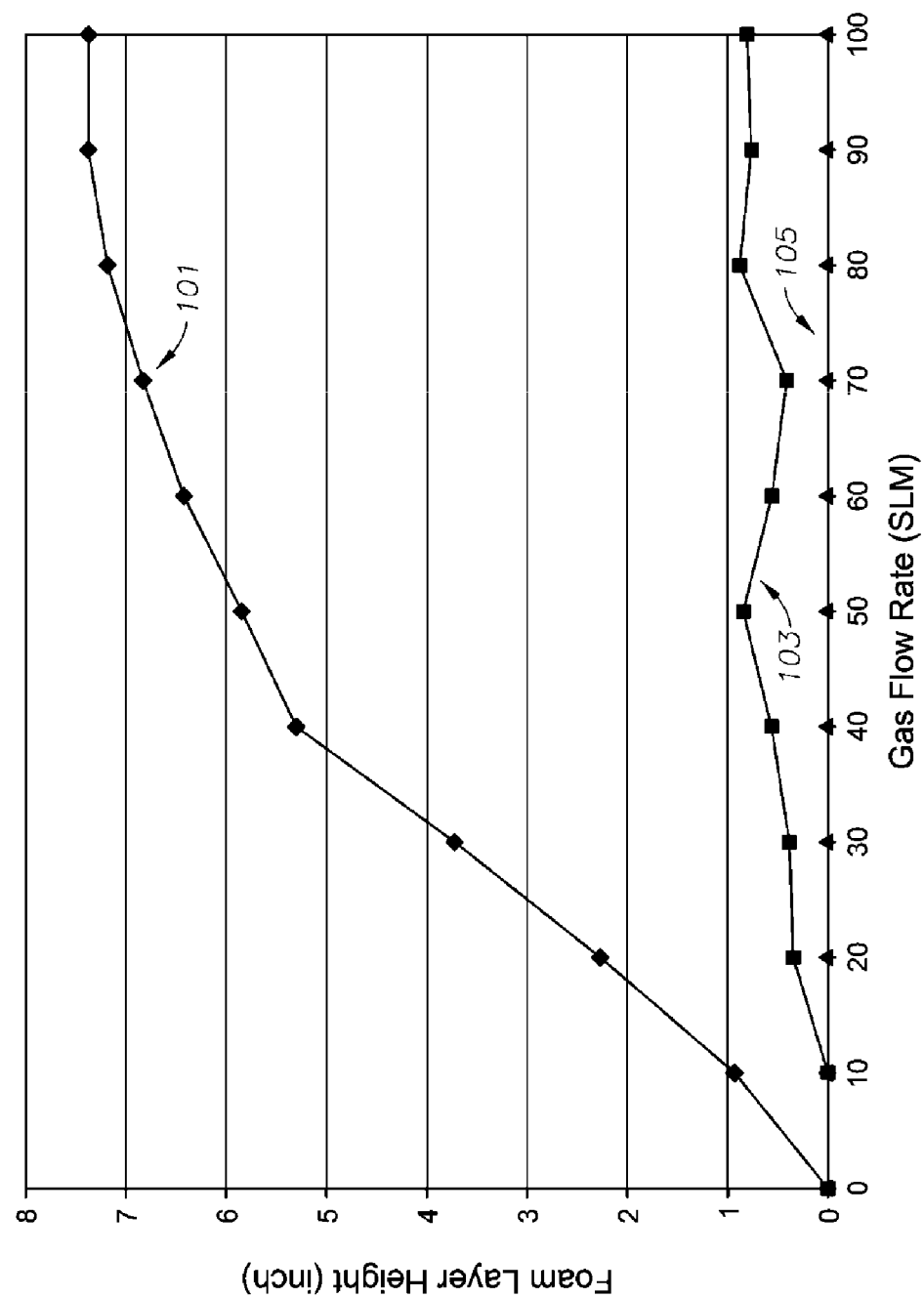

OXIDATION OF HYDROCARBONS

I. PRIORITY CLAIM

This application is a National Stage Application of International Application No. PCT/US2013/058226 filed Sep. 5, 2013, which claims the benefit of U.S. Provisional Application No. 61/698,169, filed Sep. 7, 2012, the disclosures of which is fully incorporated herein by reference.

FIELD

The present invention relates to a process for oxidizing hydrocarbons and, in particular, a process for oxidizing alkyl-substituted aromatic hydrocarbons in a liquid phase by oxygen. The present invention is useful, e.g., in making phenol and/or cyclohexanone by oxidation of cyclohexylbenzene to produce hydroperoxide thereof and subsequent cleavage thereof.

BACKGROUND

The oxidation of hydrocarbons is an important reaction in industrial organic chemistry. For example, the oxidation of cyclohexane is used commercially to produce cyclohexanol and cyclohexanone, which are important precursors in the production of nylon, whereas oxidation of alkyl-substituted aromatic hydrocarbons is used to produce phenol, a precursor in the production of polycarbonates and epoxy resins.

Oxidation of hydrocarbons can be conducted using well-known oxidizing agents, such as $KMnO_4$, $CrO_3$, and $HNO_3$. However, these oxidizing agents have the disadvantage of being relatively expensive, and moreover their use is accompanied by the production of unwanted coupling products which can cause disposal problems and ecological pollution.

Thus, oxidizing agents based on peroxides or $N_2O$ have been used. The cheapest oxidizing agent, however, is molecular oxygen, either in pure form or as atmospheric oxygen. However, oxygen itself is usually unsuitable for oxidizing hydrocarbons, since the reactivity of the $O_2$ molecule, which occurs in the energetically favorable triplet form, is not sufficient. As such, various catalysts have been developed to mediate the oxidation of an organic substrate using $O_2$.

For example, International Publication No. WO2009/058527A1 discloses the use of a cycloimide as an effective catalyst in the oxidation of hydrocarbons to produce a hydroperoxide thereof. The use of the cycloimide catalyst, especially N-hydroxyphthalimide (NHPI), was found to be particularly conducive to a high oxidation conversion of the hydrocarbon and the selectivity of certain desired hydroperoxides. This reference also discloses the reclamation and recycle of the cycloimide catalyst from the reaction mixture.

The oxidation reaction of hydrocarbons by $O_2$ is typically conducted in a bubble column reactor to which a liquid mixture comprising the hydrocarbon to be oxidized is fed, through which a stream of $O_2$-containing gas, such as air or pure $O_2$, is bubbled. The stream of gas is desirably introduced into the liquid mixture in proximity to the bottom, forming bubbles traveling through the column so that there is sufficient contact between the $O_2$ and the hydrocarbon molecules. While the $O_2$ bubbles travel upwards, they tend to agitate the liquid, resulting in better mixing of the whole reaction system. On the other hand, it was also observed that, in certain reaction systems, such as those using pure hydrocarbons as the reactants, at and/or close to the beginning of the oxidation process, a substantial amount of foam can be generated atop the liquid mixture by the agitation. The presence of a thick layer of foam can be detrimental to the oxidation operation for various reasons.

Hence, there is a need for an improved oxidation process for hydrocarbons with suppressed foaming at least at and/or close to the beginning of the oxidation operation.

SUMMARY

The present inventors discovered that, by introducing a relatively small concentration of a hydroperoxide material into the oxidation reaction medium inside the oxidation reactor at and/or close to the beginning of the oxidation process, one can significantly reduce the amount of foam produced when a stream of $O_2$-containing gas is bubbled through the reaction medium. The present invention is largely based on this discovery.

Thus, a first aspect of the present disclosure resides in a process for oxidizing a first hydrocarbon, the process comprising:
(S-I) feeding a first feedstock comprising the first hydrocarbon into an oxidation reactor to obtain a reaction medium;
(S-II) contacting the reaction medium with a gas stream comprising $O_2$ in the oxidation reactor; and
(S-III) supplying a hydroperoxide additive to the oxidation reactor such that the total concentration of hydroperoxide compound(s) in the reaction medium is in a range from 3.1 wt % to 20.0 wt %, based on the total weight of the reaction medium in the oxidation reactor.

A second aspect of the present disclosure resides in a process for making cyclohexanone and/or phenol, the process comprising the following steps:
(S-A) contacting benzene and $H_2$ with a hydroalkylation catalyst under a hydroalkylation condition effective to produce a hydroalkylation effluent comprising cyclohexylbenzene;
(S-B) oxidizing at least a portion of the cyclohexylbenzene in the hydroalkylation effluent in an oxidation reactor to produce an oxidation reaction effluent comprising cyclohexylbenzene hydroperoxide by:
(S-BI) feeding a first feedstock comprising the at least a portion of the cyclohexylbenzene into the oxidation reactor to obtain a reaction medium;
(S-BII) contacting the reaction medium with a gas stream comprising $O_2$ in the oxidation reactor; and
(S-BIII) supplying a hydroperoxide additive to the oxidation reactor such that the total concentration of hydroperoxide compound(s) is in a range from 0.5 wt % to 20.0 wt %, based on the total weight of the reaction medium in the oxidation reactor; and
(S-C) subjecting at least a portion of the cyclohexylbenzene hydroperoxide in the oxidation reaction effluent to a cleavage reaction to obtain a cleavage effluent comprising cyclohexanone and phenol.

Embodiments of the present disclosure have one or more of the following advantages. First, by employing even a relatively low concentration of a hydroperoxide additive in the reaction medium at and/or close to the beginning of the oxidation process, one can surprisingly suppress the amount and severity of foam generated atop the reaction medium, resulting in less interference to the process. Second, the suppression of foaming allows for accurate measurement of the operating level of the gas-liquid mixture and proper control and adjustment of the process parameters. Third, the reduced foaming results in better mixing and reaction between $O_2$ and the first hydrocarbon and hence higher overall production efficiency. Fourth, the suppression of foam increases the utilization rate of the internal space of the reactor. Fifth, the suppression of foam formation at and/or close to the beginning of the oxidation reaction can significantly shorten the time required for the reactor to reach a steady state, and thereby increase the overall productivity of the manufacturing process.

Additional features and advantages of the invention will be set forth in the detailed description and claims, as well as the appended drawings. It is to be understood that the foregoing general description and the following detailed description are merely exemplary of the invention, and are intended to provide an overview or framework to understanding the nature and character of the invention as it is claimed.

BRIEF DESCRIPTION OF THE DRAWINGS

FIG. 1 is a diagram showing the initial height of the foam layers in a cyclohexylbenzene oxidation reactor at various initial average concentrations of cyclohexyl-1-phenyl-1-hydroperoxide used as a defoaming agent as a function of the flow rate of the $O_2$-containing gas stream bubbled through the reaction medium.

DETAILED DESCRIPTION OF THE EMBODIMENTS

In the present disclosure, a process is described as comprising at least one "step." It should be understood that each step is an action or operation that may be carried out once, or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydroperoxide additive" include embodiments where one, two or more different types of the hydroperoxide additive are used, unless specified to the contrary or the context clearly indicates that only one type of the hydroperoxide additive is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. All ranges expressed herein should include both end points as two specific embodiments unless specified or indicated to the contrary.

The terms "group," "radical," and "substituent" are used interchangeably in the present disclosure. For purposes of this disclosure, "hydrocarbyl radical" is defined to be a radical, which contains hydrogen atoms and up to 20 carbon atoms and which may be linear, branched, or cyclic, and when cyclic, aromatic or non-aromatic. "Substituted hydrocarbyl radicals" are radicals in which at least one hydrogen atom in a hydrocarbyl radical has been substituted with at least one functional group or where at least one non-hydrocarbon atom or group (i.e., a hetero atom or group) has been inserted within the hydrocarbyl radical, either in a side chain/group or the backbone.

The term "MCM-22 family material" (or "material of the MCM-22 family" or "molecular sieve of the MCM-22 family" or "MCM-22 family zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Molecular sieves of the MCM-22 family are preferred as the alkylation catalyst since they have been found to be highly selective to the production of sec-butylbenzene, as compared with the other butylbenzene isomers. Molecular sieve UZM-8 (described in U.S. Pat. No. 6,756,030) may be used alone or in conjunction with a MCM-22 family molecular sieve. Desirably, the molecular sieve is selected from (a) MCM-49, (b) MCM-56 and (c) isotypes of MCM-49 and MCM-56, such as ITQ-2.

The present invention provides a process for oxidizing a first hydrocarbon to produce a first oxygenate, such as an alcohol, ether, ketone, aldehyde, carboxylic acid, dicarboxylic acid, ester, hydroperoxide, peracid, or combination or mixture of at least two thereof. In one particularly advantageous embodiment, the processes of the present disclosure are used for making a first hydroperoxide of the first hydrocarbon.

As discussed above, the oxidation of an alkyl-substituted aromatic compound to produce an oxygenate thereof can be advantageously conducted in a bubble column reactor, where an $O_2$-containing gas stream is bubbled through the feedstock liquid comprising the hydrocarbon. However, we have found that a substantial amount of foam can be generated at least at and/or close to the beginning of the oxidation reaction inside the bubble column oxidation reactor. A foam layer is a low density band of small bubbles with liquid sparsely mixed in, usually resting atop the reaction medium inside the reactor. A dividing line between the foam layer and the adjacent liquid layer is normally visible due to the markedly different densities and optical behaviors of the two layers. Foam formation reduces the amount of useful reactor volume for process throughput and any foam reduction will improve reactor utilization. Foam formation can lead to level instabilities, making the reactor difficult to effectively control. The foaming problem can be especially pronounced where the reaction medium comprises an alkyl-substituted aromatic compound such as cyclohexylbenzene. The foam layer lying atop the feedstock liquid can accumulate to a significant thickness, thereby hindering the operation of the oxidation process. For example, in certain embodiments, one may install a differential pressure instrument having two sensor legs in the bubble column in proximity to the projected level of the reaction medium surface, with the lower sensor below the projected level, and the upper sensor above the projected level, by which the actual reaction medium surface level is measured. The measured pressure information can be used to control and adjust other process parameters inside the oxidation column, such as temperature, flow rate of the liquid feedstock, flow rate of the $O_2$-containing gas stream, pressure inside the oxidation reactor, and the like. The presence of substantial foam at the location of the projected level of the reaction medium upper surface can lead to erroneous reading by the sensors and hence improper or even failed process control. In other embodiments, one may install an observation window on the wall of the bubble column in proximity to the top surface of the reaction medium to dynamically observe the reaction medium height and reaction behavior inside the column. The foam accumulating at the location of the observation window will substantially interfere with accurate observation from the outside. Therefore, there is a substantial need of suppressing foaming during the oxidation reaction inside the bubble column.

The present inventors have surprisingly found that by including even a relatively low concentration of a hydroperoxide additive at and/or close to the beginning of the oxidation operation inside the bubble column, foaming at and/or close to the beginning of the oxidation reaction can be substantially suppressed. The hydroperoxide additive used as the defoaming agent at and/or close to the beginning of the oxidation can be the same as or different from a part or the entirety of the first oxygenate produced by oxidizing the first hydrocarbon (e.g., an alkyl-substituted aromatic compound) in the feedstock liquid intended for oxidation. As the oxidation reaction progresses, the concentration of the first oxygenate in the reaction medium increases, and as a result, foaming can present much less an issue than at and/or close to the beginning of the reaction.

The First Hydrocarbon

Using the present process a wide group of substituted or unsubstituted saturated or unsaturated hydrocarbons, such as alkanes, cycloalkanes, alkenes, cycloalkenes, and aromatics, can be selectively oxidized. Particularly, the processes of the various aspects and embodiments of the present disclosure can be advantageously used to oxidize alkyl-substituted aromatic compounds to make, among others, a hydroperoxide thereof. For example, the process has utility in the selective oxidation of isobutane to tertiary butyl hydroperoxide and tertiary butanol, the selective oxidation of cyclohexane to cyclohexyl hydroperoxide, cyclohexanol and cyclohexanone, and the selective oxidation to the corresponding hydroperoxides of alkyl-substituted aromatic compounds of the general formula (F-I) below:

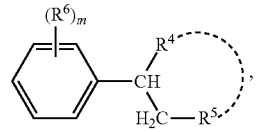

(F-I)

wherein $R^4$ and $R^5$ each independently represents hydrogen or an alkyl group having from 1 to 4 carbon atoms, or $R^4$ and $R^5$, defined above, join together via a covalent bond, as indicated by the dotted line, to form a cyclic group having from 4 to 10 carbon atoms with the adjacent linkage —CH—CH$_2$—, the cyclic group being optionally substituted; $R^6$, the same or different at each occurrence, each independently represents a substituent on the phenyl ring selected from hydrogen, an alkyl group having from 1 to 4 carbon atoms and a cyclohexyl group; m is an integer from 1 to 5; and the first hydrocarbon is oxidized to produce a first oxygenate which is a first hydroperoxide of the first hydrocarbon represented by the following general formula (F-II):

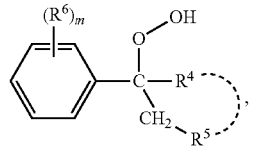

(F-II)

wherein $R^4$, $R^5$, $R^6$ and m have the same meaning as in formula (F-I).

In certain embodiments, the alkyl-substituted aromatic compound of general formula (F-I) is selected from ethyl benzene, cumene, sec-butylbenzene, sec-pentylbenzene, p-methyl-sec-butylbenzene, 1,4-diphenylcyclohexane, sec-hexylbenzene, and cyclohexylbenzene, and in certain specific embodiments, the first hydrocarbon is oxidized to produce a first oxygenate which is a hydroperoxide of the alkyl-substituted aromatic compound, correspondingly selected from ethyl benzene hydroperoxide, cumene hydroperoxide, sec-butylbenzene hydroperoxide, sec-pentylbenzene hydroperoxide, p-methyl-sec-butylbenzene hydroperoxide, 1,4-diphenylcyclohexane hydroperoxide, sec-hexylbenzene hydroperoxide, and cyclohexylbenzene hydroperoxide.

Non-limiting examples of suitable alkyl-substituted aromatic compounds are ethyl benzene, cumene, sec-butylbenzene, sec-pentylbenzene, p-methyl-sec-butylbenzene, 1,4-diphenylcyclohexane, sec-hexylbenzene, and cyclohexylbenzene, with sec-butylbenzene and cyclohexylbenzene being preferred.

In one practical embodiment, the alkyl-substituted aromatic compound of general formula (F-I) is sec-butylbenzene and is produced by alkylating benzene with at least one $C_4$ alkylating agent under alkylation conditions and in the presence of a heterogeneous catalyst, such as zeolite Beta or desirably at least one molecular sieve of the MCM-22 family (as defined below) in certain embodiments. The alkylation conditions can include a temperature of from 60° C. to 260° C., for example from 100° C. to 200° C. The alkylation pressure can be 7000 kPa or less, for example from 1000 kPa to 3500 kPa. The alkylation can be carried out at a weight hourly space velocity (WHSV) based on $C_4$ alkylating agent in a range from 0.1 $hr^{-1}$ to 50 $hr^{-1}$, for example from 1 $hr^{-1}$ to 10 $hr^{-1}$.

The $C_4$ alkylating agent may comprise at least one linear butene, namely butene-1, butene-2 or a mixture thereof. The alkylating agent can also be an olefinic $C_4$ hydrocarbon mixture containing linear butenes, such as can be obtained by steam cracking of ethane, propane, butane, LPG and light naphthas, catalytic cracking of naphthas and other refinery feedstocks and by conversion of oxygenates, such as methanol, to lower olefins. For example, the following $C_4$ hydrocarbon mixtures are generally available in refinery plants employing steam cracking to produce olefins and are suitable for use as the $C_4$ alkylating agent: a crude steam cracked butene stream, Raffinate-1 (the product remaining after solvent extraction or hydrogenation to remove butadiene from the crude steam cracked butene stream), and Raffinate-2 (the product remaining after removal of butadiene and isobutene from the crude steam cracked butene stream).

In a further practical embodiment, the alkyl-substituted aromatic compound of general formula (F-I) is cyclohexylbenzene and is produced by contacting benzene with hydrogen in the presence of a heterogeneous bifunctional catalyst which comprises at least one metal having hydrogenation activity, typically selected from the group consisting of palladium, ruthenium, nickel, cobalt, and a crystalline inorganic oxide material having alkylation activity, typically at least one molecular sieve of the MCM-22 family (as defined below). The contacting step can be conducted at a temperature in a range from 50° C. to 350° C. The contacting pressure may be, e.g., in a range from 100 kPa to 7000 kPa. The benzene to hydrogen molar ratio in the contacting step may be, e.g., in a range from 0.01 to 100. The WHSV during the contacting step can be, e.g., in the range of from 0.01 to 100.

The First Oxygenate

The product of the present oxidation process, the first oxygenate, depends in part on the nature of the first hydrocarbon substrate being oxidized. Examples of the first oxygenate include, but are not limited to, alcohol, ether, ketone, aldehyde, carboxylic acid or dicarboxylic acid, esters, hydroperoxide, peracid, or any other compound comprising one or more oxygen atoms in its molecular structure. While it is desirable in many reactions that only one, or a very small number of, oxygenate species is produced, in reality, a mixture of a plurality of different oxygenate species may be produced in an oxidation reaction. Thus, producing a mixture of one or more oxygenate species mentioned above is deemed within the scope of the present invention. In a particularly advantageous embodiment, the first oxygenate comprises a first hydroperoxide.

For example, when the first hydrocarbon (as a "substrate" for oxidation) is isobutane, the first oxygenate as the oxidation product may comprise tertiary butyl hydroperoxide (which is useful as an oxidizing agent for, e.g., olefin epoxidation) and tertiary butanol (which is useful as a gasoline additive).

For another example, when the first hydrocarbon is cyclohexane, the first oxygenate as the oxidation product may comprise cyclohexyl hydroperoxide, cyclohexanol and cyclohexanone. Cyclohexyl hydroperoxide is readily decomposed to additional cyclohexanol and cyclohexanone, either thermally or with the assistance of a catalyst. Cyclohexanol can be oxidized with aqueous nitric acid to produce adipic acid, which is a precursor in the synthesis of nylon-6,6, whereas cyclohexanone can be converted to cyclohexanoxime which undergoes acid-catalyzed rearrangement to produce caprolactam, a precursor in the synthesis of nylon-6.

Where the first hydrocarbon is an alkyl-substituted aromatic compound of the general formula (F-I) above, a desirable product of the oxidation reaction in certain embodiments is a hydroperoxide of general formula (F-II) defined above. Desirably, the hydroperoxide is sec-butylbenzene hydroperoxide or a cyclohexylbenzene hydroperoxide, e.g., cyclohexyl-1-phenyl-1-hydroperoxide illustrated by the following formula (F-V) in certain embodiments:

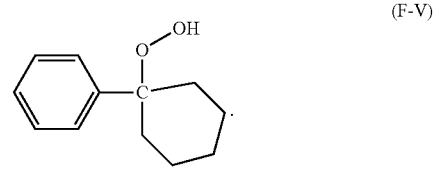

(F-V)

The hydroperoxide of the general formula (F-II) can then be converted by acid cleavage to phenol or a substituted phenol and an aldehyde or ketone of the general formula $R^4COCH_2R^5$ (F-VI), in which $R^4$ and $R^5$ have the same meaning as in formula (F-II). Phenol can be reacted with acetone to produce bisphenol A, a precursor in the production of polycarbonates and epoxy resins.

The Hydroperoxide Additive

In the processes of the present disclosure, a certain amount of a hydroperoxide additive, which is a derivative of a second hydrocarbon, is supplied to the oxidation reactor to function as a de-foaming agent at and/or close to the beginning of the oxidation reaction in the reaction medium. Without intending to be bound by any particular theory, it is believed that the hydroperoxide additive alters the surface energy of the reaction medium in the oxidation reactor in a manner similar to a surfactant or traditional defoaming agent, and thereby promotes the coalescence of the bubbles and reduces the formation of foams and bubbles at the top surface of the reaction medium when a stream of gas is bubbled through the reaction medium in the oxidation reactor. While conventional defoaming agents such as mineral oil, silicone oil and the like may be added into the first feedstock and/or the reaction medium to suppress foam formation, they can interfere with the desired oxidation reaction, causing unwanted side reactions and by-products, and/or leading to difficulties in later-stage product purification. The hydroperoxide additive, on the other hand, normally would not cause such undesirable effect to the oxidation of the first hydrocarbon. This is especially true where the first hydrocarbon and the second hydrocarbon are analogous compounds, such as where both are alkyl-substituted aromatic compounds. In particularly advantageous embodiments, the first hydrocarbon and the second hydrocarbon are the same compound. In especially advantageous embodiments, the first oxygenate and the hydroperoxide additive are the same compound. In these embodiments, because the hydroperoxide additive is a desired product of the oxidation reaction of the first hydrocarbon, the addition thereof into the first feedstock and/or the reaction medium as a defoaming agent would not cause any contamination issue at all.

To the extent the first hydrocarbon and the second hydrocarbon, and the first oxygenate and the hydroperoxide additive, may be analogous or even identical as mentioned above, the above description of the first hydroperoxide of the first hydrocarbon can be adapted for the hydroperoxide additive. Where the second hydrocarbon is an alkylated aromatic compound, such as one represented by the formula (F-I) described above in connection with the first hydrocarbon, the hydroperoxide additive can be a corresponding hydroperoxide thereof, such as one represented by the formula (F-II) described above in connection with the first hydrocarbon. Therefore, non-limiting examples of the hydroperoxide additive include: ethyl benzene hydroperoxide, cumene hydroperoxide, sec-butylbenzene hydroperoxide, sec-pentylbenzene hydroperoxide, p-methyl-sec-butylbenzene hydroperoxide, 1,4-diphenylcyclohexane hydroperoxide, sec-hexylbenzene hydroperoxide, and cyclohexylbenzene hydroperoxide, e.g., the hydroperoxide of formula (F-V) above.

At least a part of the hydroperoxide additive is included in the feedstock and/or the reaction medium before an $O_2$-containing gas has contacted with the feedstock and/or the reaction medium (e.g., by passing the gas stream through the reaction medium) in the oxidation reactor for T hours, where in various embodiments T is: 5.0; 4.5; 4.0; 3.5; 3.0; 2.5; 2.0; 1.5; 1.0; 0.75; 0.50; 0.25; 0.10; or even 0.05. In certain embodiments, all of the hydroperoxide additive is included in the first feedstock and/or the reaction medium before an $O_2$-containing gas stream has been in contact with the reaction medium (e.g., by passing through the reaction medium) for T hours, where in various embodiments T is: 5.0; 4.5; 4.0; 3.5; 3.0; 2.5; 2.0; 1.5; 1.0; 0.75; 0.50; 0.25; 0.10; or 0.05. In one embodiment, all of the hydroperoxide additive is included into the first feedstock before the first feedstock is charged into the oxidation reactor. In another embodiment, at least part of the hydroperoxide additive and the remainder of the first feedstock are charged into the oxidation reactor at different locations, and then mixed before an $O_2$-containing gas stream has been in contact with the reaction medium (e.g., by passing through the reaction medium) for T hours, where in various embodiments T is: 5.0; 4.5; 4.0; 3.5; 3.0; 2.5; 2.0; 1.5; 1.0; 0.75; 0.50; 0.25; 0.10; or 0.05. It is highly desired, though not required, that the hydroperoxide additive is substantially uniformly distributed in the first feedstock and/or the reaction medium before the $O_2$-containing gas stream has been in contact with the reaction medium (e.g., by passing through the reaction medium) for T hours, where in various embodiments T is 5.0; 4.5; 4.0; 3.5; 3.0; 2.5; 2.0; 1.5; 1.0; 0.75; 0.50; 0.25; 0.10; or 0.05. An oxidation reaction may have already occurred, though typically to a small, and sometimes negligible degree, before the $O_2$-containing gas stream has started passing through the reaction medium. This is because the reaction medium may have contacted $O_2$ molecules due to exposure to the ambient atmosphere before the $O_2$-containing gas stream is passed through the reaction medium.

To impart the desired level of foaming suppression, the initial average concentration of the hydroperoxide additive in the reaction medium in the oxidation reactor, CHPXD(1), defined as the average concentration thereof in the reaction medium within the first three hours from the moment the $O_2$-containing gas stream starts to pass through the reaction medium, is at least 0.5 wt % of the reaction medium in the reactor in certain embodiments. Below this concentration, some defoaming effect may be observed but it may be insufficient to permit fast start-up of the oxidation reactor. Without using a defoaming agent such as the hydroperoxide additive, it may take a long time, such as over 10 hours, before the foam layer atop the reaction medium reduces to a stable level. Many oxidation processes are slow in nature and can be a speed-limiting step in the industrial manufacture of many important chemicals. Shortening the time required to achieve a substantially stable oxidation reaction in the oxidation reactor therefore can have significant economic impact on the overall process. Higher CHPXD(1) may be used to achieve the desired foam suppression in a desired period of time, e.g., in certain embodiments CHPXD(1)≥X wt %, where X in various embodiments may be: 0.6; 0.8; 1.0; 1.5; 2.0; 2.5; 3.0; 3.1; 3.5; 4.0; 5.0; 6.0; 7.0; 8.0; 9.0; and 10.0.

Certain hydroperoxides can pose a risk at a high concentration due to their unstable nature and thus are undesirable for storage and transportation. When such hydroperoxide is used as the hydroperoxide additive, it is particularly desired that it is produced in situ in the same facility where the oxidation reaction of the present disclosure is carried out. Nonetheless, where possible, higher CHPX(1) such as 20 wt %, 18 wt %, 16 wt %, 15 wt %, 14 wt %, 12 wt %, or 10 wt % may be used at and/or close to the beginning of step (S-II) or step (S-BII). However, if CHPXD(1) is too high, the oxidation reaction can be interfered by side reactions and byproducts from the hydroperoxide additive. For example, where the hydroperoxide additive is cyclohexylbenzene hydroperoxide, and the first oxygenate is cyclohexylbenzene hydroperoxide, it was found that the selectivity of the oxidation reaction of cyclohexylbenzene to cyclohexyl-1-phenyl-1-hydroperoxide can be reduced to a undesirable level if CHPXD(1) is too high, e.g., CHPXD(1)>25.0 wt %. Thus, it is desired that CHPXD(1)≤YY wt %, where in various embodiments YY can be: 20.0; 18.0; 16.0; 14.0; 12.0; or even 10.0.

The hydroperoxide additive is advantageously used at a low concentration in the oxidation process according to the present disclosure. A small initial average concentration of the hydroperoxide additive at up to 8.0 wt % of the reaction medium was sufficient to suppress the foam layer to a negligible level in certain embodiments. Depending on the reaction, the desired minimal level of the foam layer, and the desired time to achieve the minimal level of the foam layer, one may choose CHPXD(1)≤ZZ wt %, where ZZ in certain embodiments may be: 8.0; 6.0; 5.0; 4.0; 3.0; 2.0; or even 1.5. A low CHPXD(1) is particularly desirable where (i) the first oxygenate is not identical with the hydroperoxide additive, or (ii) the hydroperoxide additive is not converted into the first oxygenate during the oxidation step or a subsequent step, to minimize the effect of the hydroperoxide additive as a potential contaminant.

As a result of the addition of the hydroperoxide additive to the reactor before, at or shortly after the time the $O_2$-containing gas starts to contact the reaction medium (e.g., by passing through the reaction medium), the total concentration of hydroperoxide compound(s) at a given time point TT in the reaction medium, including the hydroperoxide additive and any hydroperoxide compound(s) produced as a result of the reaction(s) in the reactor, the same as or different from the hydroperoxide additive, is in a range from a lower limit of C1 wt % to a higher limit of C2 wt %, where in various embodiments C1 can be: 0.1; 0.2; 0.3; 0.5; 0.8; 1.0; 1.5; 2.0; 2.5; 3.0; 3.1; 3.5; 4.0; 4.5; 5.0; 6.0; 8.0; or even 10.0; and C2 can be: 24.0; 23.0; 22.0; 21.0; 20.0; 19.0; 18.0; 17.0; 16.0; 15.0; 14.0; 13.0; 12.0; 11.0; or even 10.0. In various embodiments, TT can be 24 hours, 22 hours, 20 hours, 18 hours, 16 hours, 15 hours, 14 hours, 12 hours, 10 hours, 8 hours, 6 hours, 5 hours, 4 hours, 3 hours, 2 hours, 1 hour, or even 0.5 hour, after the moment when $O_2$-containing gas stream starts to contact the reaction medium (e.g., by passing the gas stream through the reaction medium).

Hydrocarbon Oxidation

In addition to the first hydrocarbon and the hydroperoxide additive, the first feedstock and/or the reaction medium may comprise other components, such as an inert solvent. To that end, an inert third hydrocarbon may be included in the first feedstock or introduced into the oxidation reactor separately. The use of a solvent can increase the solubility of the catalyst(s) used, such as the one represented by formula (F-III) described above, and facilitate the management of mass transfer and heat transfer. Non-limiting examples of the third hydrocarbon, especially where the first hydrocarbon is an alkyl-substituted aromatic compound, such as one represented by formula (F-I) above, include: pentane; hexane; heptane; cyclohexane; cyclopentane; cycloheptane; dodecane; decane; cyclododecane; benzene; methyl benzene; ethyl benzene; xylene; and the like.

The contacting oxidation step in the present processes can be advantageously accomplished by contacting the reaction medium comprising the first hydrocarbon to be oxidized (e.g., an alkyl-substituted aromatic substrate) with an oxygen-containing gas in the presence of a catalyst comprising a cyclic imide of the general formula (F-III) below:

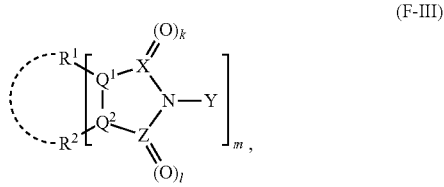

(F-III)

wherein each of $R^1$ and $R^2$, the same or different, is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I, or $R^1$ and $R^2$, defined above in this paragraph, can be linked to one another via a covalent bond indicated by the dotted line to form a cyclic moiety with $Q^1$ and $Q^2$, defined below;

each of $Q^1$ and $Q^2$, the same or different, is independently selected from C, CH and $CR^3$;

each of X and Z is independently selected from C, S, $CH_2$, N, P and elements of Group 4 of the Periodic Table;

Y is O or OH;

k is 0, 1 or 2;

l is 0, 1 or 2;

m is 1, 2 or 3; and $R^3$ can be selected from selected from hydrocarbyl and substituted hydrocarbyl radicals having 1 to 20 carbon atoms, $SO_3H$, $NH_2$, OH, $NO_2$, H, F, Cl, Br and I.

Advantageously, each of $R^1$ and $R^2$ is independently selected from aliphatic alkoxy or aromatic alkoxy radicals, carboxyl radicals, alkoxy-carbonyl radicals and hydrocarbon radicals, each of which radicals has 1 to 20 carbon atoms.

In certain embodiments, the cyclic imide of the general formula (F-III) obeys the following general formula (F-IV):

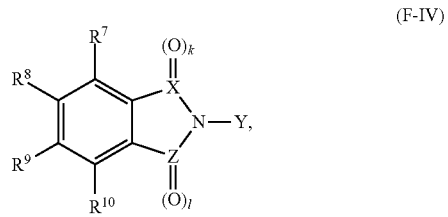

(F-IV)

wherein each of $R^7$, $R^8$, $R^9$ and $R^{10}$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I;

each of X and Z is independently selected from C, S, $CH_2$, N, P and an element of Group 4 of the Periodic Table;

Y is O or OH;

k is 0, 1 or 2; and l is 0, 1 or 2.

In certain embodiments, each of $R^7$, $R^8$, $R^9$ and $R^{10}$ is independently selected from aliphatic alkoxy or aromatic alkoxy radicals, carboxyl radicals, alkoxy-carbonyl radicals and hydrocarbon radicals, each of which radicals have 1 to 20 carbon atoms.

Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Another suitable catalyst is N,N',N'''-trihydroxyisocyanuric acid. In one particularly advantageous embodiment, the cyclic imide catalyst comprises NHPI.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N'''-trihydroxyisocyanuric acid is employed in an amount from 0.0001 wt % to 15 wt %, such as from 0.001 wt % to 5 wt %, of the first hydrocarbon (e.g., cyclohexylbenzene).

Oxidation of a hydrocarbon to produce a corresponding hydroperoxide thereof is described in, e.g., WO2009/058527A1, the relevant parts thereof are incorporated herein by reference in their entirety.

The $O_2$-containing gas stream may be pure $O_2$, air, $O_2$-enriched air, $N_2$-enriched air, $O_3$-enriched air, and the like. In certain embodiments, especially where a catalyst represented by formula (F-III), particularly formula (F-IV), especially NHPI, is used, it is desired that the first feedstock is substantially dry, and that the $O_2$-containing gas stream is substantially dry as well. This is because the catalyst may undergo undesired reaction, such as hydrolysis, when water is present.

In certain embodiments, the $O_2$-containing gas stream is advantageously introduced into the reaction medium at a location in proximity to the bottom of the oxidation reactor. The $O_2$-containing gas stream generates a large number of bubbles inside the reaction medium in the oxidation reactor. The travel of the gas stream upward from the bottom to the top surface of the reaction medium will facilitate $O_2$ mass transfer, allowing sufficient contact time between the first hydrocarbon and $O_2$ molecules, stir the reaction medium, leading to better mixing, mass transfer and heat transfer. In the absence of foaming, the bubbles establish an equilibrium diameter rapidly which is maintained throughout most of the column. Bubble volume is reduced through mass transfer of $O_2$ from the gas to the liquid, but bubbles can then recombine to maintain the same basic size. This leads to a decline in the number of bubbles. As mentioned above, the addition of the hydroperoxide additive into the first feedstock and/or the reaction medium surprisingly facilitates the coalescence of the ascending bubbles and reduces the number of bubbles and thereby suppressing foam formation and accumulation atop the surface of the reaction medium.

The oxidation reactor may be a continuous reactor into which the first feedstock is continuously charged and an oxidation reaction effluent is continuously withdrawn once the reaction has reached a steady state. Alternatively, the oxidation reactor may be a batch reactor, into which the first feedstock is charged, allowed to react until completion of a cycle, and then the reaction medium is withdrawn as an oxidation reaction effluent. Alternatively, the oxidation reactor may be a semi-batch reactor known in the art. In certain embodiments, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, e.g., by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of the first hydrocarbon or oxygen, or both, in each. Where a plurality of oxidation reactors are used in series, it is desired that the process of the present disclosure utilizing a hydroperoxide additive as the defoaming agent is used in at least the very first reactor. In such embodiments, the feed into the down-stream reactor(s), which comprises at least a portion of the effluent from the oxidation reactor, would comprise the hydroperoxide additive and/or the first oxygenate, which can function as defoaming agent. Therefore, in the serial reactor configuration, foaming in the downstream reactors is less of an issue than in the very beginning reactor. However, it is also possible that one may add the hydroperoxide additive into reactors other than the very first oxidation reactor, in an effort to suppress foaming in the downstream reactors to a desired degree.

The conditions used to effect the oxidation step can vary significantly with the type of first hydrocarbon oxidation substrate to be oxidized. Typically, the higher the temperature of the reaction medium, the faster the reaction and the higher the conversion of the first hydrocarbon to the first hydrogenate. However, normally, if over a certain optimal limit, the higher the temperature of the reaction medium, the more intense undesired side reactions may occur and the more by-products may be produced, and hence the lower the selectivity of the oxidation reaction toward the desired first oxygenate becomes. The temperature of the reaction medium can affect the viscosity and surface energy thereof, hence its ability to form foam and the severity of the foam problem. Thus, suitable temperature of the reaction medium and/or the feedstock in step (S-II) or step (S-BII) may range from a lower limit Tl to a higher limit Th. Non-limiting examples of Tl include: 20° C., 30° C., 40° C., 50° C., 60° C., 70° C., 80° C., 90° C., 100° C.; and non-limiting examples of Th include: 150° C., 140° C., 130° C., 120° C., 110° C., 100° C., 90° C., as long as Th>Tl.

The contacting step (S-II) or (S-BII) may be carried out at an absolute pressure inside the reactor in a range from a lower limit Pl to a higher limit Ph. Non-limiting examples of Pl include: 15 kPa; 30 kPa; 50 kPa; 80 kPa; and 100 kPa; and non-limiting examples of Ph include: 2000 kPa; 1500 kPa; 1000 kPa; 800 kPa; 500 kPa; 300 kPa; 200 kPa; 150 kPa; 120 kPa; 100 kPa; as long as Pl<Ph. At a higher pressure of the gas stream passing through the reaction medium, better $O_2$ mass transfer can be achieved and more $O_2$ can be made available for the oxidation reaction in a given volume of the reaction medium at any given time. Thus, in certain embodiments, it is desired that the internal pressure in the oxidation reactor is at least P1 kPa, where P1 in various embodiments can be: 30; 50; 80; 101; 120; and 150. However, a lower absolute pressure inside the oxidation reactor can lead to faster, more efficient and effective removal of certain by-products and contaminants in the reactor, such as water and low boiling point acids, which may react with the catalysts, especially those represented by the formula (F-IV), particularly NHPI, leading to reduction of catalytic effect such as conversion and selectivity of the oxidation reaction in the desired direction, hence an internal pressure of at most P2 kPa is desired, where P2 in various embodiments can be: 500; 400; 300; 200; 150; and 120.

The flow rate of the $O_2$-containing gas stream passing through the reaction medium in the process according to the present disclosure can be chosen depending on the nature of the first hydrocarbon and concentration thereof in the reaction medium, the oxidation reaction rate, the temperature of the reaction medium, internal pressure in the oxidation reactor, and the like. To achieve the desired oxidation rate without causing overly violent stirring in the reactor, the flow rate of the $O_2$-containing gas stream passing through the reaction medium in step (S-II) or step (S-BII) can be in a range of from a lower limit FR(1) to an upper limit FR(2), as long as FR(1)<FR(2). Non-limiting examples of FR(1) in term of volume of the gas stream (in cubic meters) passing through one kilogram of the reaction medium per minute ($m^3 \cdot min^{-1} \cdot kg^{-1}$) include: 2, 4, 5, 6, 8, 10, 15, 20, 25, 30, 35, 40, 45, 50, 55, 60, 65, 70, 75, and 80; and non-limiting examples of FR(2) in the same unit include: 100, 95, 90, 85, 80, 75, 70, 65, 60, 55, 50, 45, and 40.

As a result of the addition of the hydroperoxide additive in the reaction medium and/or the first feedstock as a defoaming agent, foaming at and/or close to the beginning of the oxidation reaction when the $O_2$-containing gas stream is passed through the reaction medium is significantly suppressed. As such, the foam layer formed atop the reaction medium may be negligible. Even if a foam layer forms atop the reaction medium at and/or close to the beginning of step (S-II) or step (S-BII), the foam layer has an average height HH1 in the first 24 hours of step (S-II) or step (S-BII), where HH1≤aa cm, where in various embodiments aa can be: 30; 25; 20; 15; 10; 8.0; 5.0; 3.0; 2.0; and even 1.0. In certain embodiments, a foam layer forms atop the reaction medium at least at and/or close to the beginning of step (S-II) or (S-BII), the foam layer having an average height HH2 in the first three hours of step (S-II) or step (S-BII), where HH2≤aa cm, where in various embodiments aa can be: 30; 25; 20; 15; 10; 8.0; 5.0; 3.0; 2.0; and even 1.0. In certain embodiments, a foam layer forms atop the reaction medium at least at and/or close to the beginning of step (S-II) or step (S-BII), the foam layer having an average height HH3 in the first 72 hours of step (S-II) or step (S-BII), where HH3≤aa cm, where in various embodiments aa can be: 30; 25; 20; 15; 10; 8.0; 5.0; 3.0; 2.0; and even 1.0.

The oxidation reactor used in the processes of the present disclosure may be advantageously equipped with a mechanical stirrer, which may be used during a part of, or the entire operation of, the oxidation reaction. In one embodiment, the mechanical stirrer is activated at least within three hours, or within two hours, or within 1 hour, or within 0.5 hour, or within 0.25 hour, or at or even before the beginning of step (S-II) or step (S-BII), such that the mechanical stirring facilitates the coalescence and collapse of the bubbles, thereby reducing or suppressing foaming.

In certain embodiments, large-size mechanical stirrers are difficult to install and maintain in an oxidation reactor with only limited free internal and/or external space available. In these embodiments, it can be advantageous to install a device such as a nozzle on the wall of the oxidation reactor capable of delivering one or more liquid jet(s) to the top surface of the reaction medium, which can facilitate the reduction and/or destruction of the foam layer, if any. The liquid jet may comprise the hydroperoxide additive, an inert solvent, a fresh stream of the first feedstock, or a recirculated reaction medium derived from the oxidation reactor. The liquid jet may work in conjunction with a mechanical stirrer or in the absence thereof.

In certain embodiments, it is highly desirable to control the amount of the reaction medium inside the oxidation reactor such that the top surface thereof is within a certain range of a projected level. To control the level of the reaction medium, one would need to measure the actual level of the liquid medium inside the reactor. A differential pressure measurement instrument with an upper and a lower sensor may be installed above and below the projected level of the liquid inside the reactor for that purpose. The pressure data measured by the sensors can be sent to a control unit, such as a computer station, where they are analyzed, and then used to control the feed amount, feed rate, discharge amount and discharge rate of the first feedstock, the hydroperoxide additive, the oxidation reaction effluent, temperature thereof, and the flow rate of the $O_2$-containing gas stream, and other reaction parameters inside the oxidation reactor. The processes in various embodiments of various aspects of the present disclosure, due to the suppressed foam formation at the top surface of the reaction medium, are particularly advantageous in utilizing such pressure sensors and the automatic control process thus enabled.

In certain embodiments of the processes of the present disclosure, it may be advantageous to install a transparent observation window on the wall of the oxidation reactor at a location in proximity to the projected level of the reaction medium, such that an operator can visually inspect and record the level of the top surface of the reaction medium and make adjustment to the operation accordingly. Due to suppressed foam formation at the top surface of the reaction medium, the processes of the present disclosure are particularly advantageous in this regard.

In embodiments of the processes according to the present disclosure where the oxidation reactor is a continuous reactor, it is highly desired that the reactor reaches steady-state operation as quickly as possible. With the facilitation of the use of the hydroperoxide additive as a defoaming agent at and/or close to the beginning of the operation, the operation may reach a steady state in a period of at most P1 hours, where P1 in various embodiments can be: 96; 84; 72; 60; 48; 36; 24; or 12. An otherwise identical, comparative, conventional process with the exception that no hydroperoxide additive is introduced into the reaction medium would normally take a period P2 to reach steady state that is typically longer than P1. In certain embodiments of the processes according to the present disclosure, P1/P2≤bb; where in various embodiments bb can be: 0.95; 0.90; 0.85; 0.80; 0.75; 0.70; 0.65; 0.60; 0.55; 0.50; 0.45; 0.40; 0.35; 0.30; 0.25; 0.20; 0.15; or even 0.10. In certain embodiments it is desired that P1/P2≥cc to avoid over stirring due to excessive flow rate of the gas stream, where cc can be: 0.20; 0.25; 0.30; 0.35; 0.40; 0.45; 0.50; 0.55; or even 0.60.

The product of the oxidation reaction of an alkylated aromatic compound (e.g., cyclohexylbenzene) can contain a first oxygenate (e.g., cyclohexyl-1-phenyl-1-hydroperoxide) at a concentration based upon the total weight of the oxidation reaction effluent from a lower limit C1 to an upper limit C2. Non limiting examples of C1 include: 5 wt %; 10 wt %; 15 wt %; 20 wt %; 25 wt % or 30 wt %; and non-limiting examples of C2 include: 80 wt %; 75 wt %; 70 wt %; 65 wt %; 60 wt %; 55 wt %; 50 wt %; 45 wt %; 35 wt %; 30 wt %; or 25%; as long as C1<C2. The oxidation reaction effluent may further comprise an oxidation catalyst (e.g., NHPI) and unreacted first hydrocarbon (e.g., cyclohexylbenzene). For example, the oxidation reaction effluent may include unreacted first hydrocarbon (e.g., cyclohexylbenzene) in an amount of at least 50 wt %, or at least 60 wt %, or at least 65 wt %, or at least 70 wt %, or at least 80 wt %, or at least 90 wt %, based upon the total weight of the oxidation reaction effluent.

Where the first oxygenate is a first hydroperoxide, at least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in unreacted first hydrocarbon (e.g., cyclohexylbenzene) and leave a residue which is concentrated in the desired hydroperoxide (e.g., cyclohexyl-1-phenyl-1-hydroperoxide) and which is subjected to the cleavage reaction. In general, however, such concentration of the hydroperoxide (e.g., cyclohexyl-1-phenyl-1-hydroperoxide) is neither necessary nor preferred. Additionally or alternatively, all or a fraction of the oxidation reaction effluent, or all or a fraction of the vacuum distillation residue may be cooled to cause crystallization of the unreacted oxidation catalyst (e.g., NHPI), which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation reaction effluent may be subjected to water washing and then passage through an adsorbent, such as a 3 Å molecular sieve, to separate water and other adsorbable compounds, and provide an oxidation composition with reduced water or oxidation catalyst content that may be subjected to the cleavage reaction. Similarly, all or a fraction of the oxidation reaction effluent may undergo a chemically or physically based adsorption, such as passage over a bed of sodium carbonate to remove the oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation reaction effluent with a liquid containing a base, such as an aqueous solution of an alkali metal carbonate or bicarbonate, to form an aqueous phase comprising a salt of the imide oxidation catalyst, and an organic phase reduced in imide oxidation catalyst. An example of separation by basic material treatment is disclosed in International Publication No. WO 2009/025939, the content of which is incorporated herein by reference in its entirety.

Cleavage Reaction

In embodiments where the first oxygenate is a hydroperoxide of the first hydrocarbon, at least a portion of the first hydroperoxide may be further subjected to a cleavage reaction to produce a ketone and a phenol or alcohol. For example, where the first hydrocarbon is cyclohexylbenzene, the first hydrogenate is cyclohexylbenzene hydroperoxide, the cyclohexylbenzene hydroperoxide may be cleaved in the presence of a catalyst to make cyclohexanone and phenol. For another example, wherein the first hydrocarbon is sec-butylbenzene, the first oxygenate is its hydroperoxide, the hydroperoxide may be cleaved to obtain phenol and butanone. A non-limiting example of suitable heterogeneous catalyst for use in the cleavage of sec-butylbenzene hydroperoxide is a smectite clay, such as an acidic montmorillonite silica-alumina clay, as described in U.S. Pat. No. 4,870,217, the entire disclosure of which is incorporated herein by reference.

In certain embodiments, the acid catalyst used in the cleavage reaction is at least partially soluble in the cleavage reaction mixture, is stable at a temperature of at least 185° C. and has a lower volatility (higher normal boiling point) than the first hydrocarbon (e.g., cyclohexylbenzene). Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a particularly advantageous catalyst in certain embodiments.

In various embodiments, the cleavage reaction mixture contains the acid catalyst at a concentration in a range from a lower limit C1 ppm to an upper limit C2 ppm based on the total weight of the cleavage reaction mixture, where C1 in various embodiments can be: 50; 100; 150; 200; 250; 300; 350; 400; 450; and 500; and C2 in various embodiments can be: 5000; 4000; 3000; 2000; 1000; 800; 500; 400; and 300; as long as C1<C2.

In other embodiments, a heterogeneous acid catalyst is employed for the cleavage reaction, such as molecular sieve, and in particular a molecular sieve having a pore size in excess of 7 Å. Examples of suitable molecular sieves include zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from 20 wt % to 80 wt % of the zeolite.

In the case of cleavage of a first hydroperoxide of an alkylated aromatic, such as cyclohexylbenzene hydroperoxide, the cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling.

In various embodiments, the cleavage reaction mixture includes the first hydrocarbon (e.g., cyclohexylbenzene) at a concentration of at least C1 wt %, based on the total weight of the cleavage reaction mixture, where C1 in various embodiments can be: 50; 55; 60; 65; 70; 75; 80; 85; or 90.

In certain embodiments, the cleavage reaction is conducted under conditions including a temperature in a range from 20° C. to 200° C., such as from 40° C. to 120° C. and a pressure in a range from 100 kPa to 2000 kPa, such as from 100 kPa to 1000 kPa, such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove heat generated. The product of the cleavage reaction is desirably a substantially equimolar mixture of the desired phenol (e.g., phenol) and ketone (e.g., cyclohexanone).

The invention will now be more particularly described with reference to the following non-limiting examples.

EXAMPLES

To a bubble column made of glass having an internal diameter of 15.24 cm was charged with 22,000 cm$^3$ of a feedstock comprising cyclohexylbenzene with a given initial concentration of cyclohexyl-1-phenyl-1-hydroperoxide. An air stream was bubbled into the column at the bottom at various gas flow rates at 21° C. and 101 kPa absolute pressure. Vigorous stirring of the liquid inside the column was observed. A high-speed video camera was used to take images of the liquid column. Foam layer height data were extracted from the images and analyzed to obtain an average foam layer height.

Data of the average foam layer height (inch) as a function of air stream flow rate (SLM, Standard Liter Per Minute) for three different initial cyclohexylbenzene hydroperoxide concentrations are reported in FIG. 1. Curve 101 corresponds to a cyclohexylbenzene hydroperoxide concentration of 0 wt %, curve 103 to a cyclohexylbenzene hydroperoxide concentration of 6.0 wt %, and curve 105 to a cyclohexylbenzene hydroperoxide concentration of 23 wt %.

FIG. 1 clearly shows that a thick layer of foam was created when no cyclohexylbenzene hydroperoxide was included in cyclohexylbenzene (curve 101) even at a moderate flow rate of the air stream, and at 6 wt %, a relatively small concentration of cyclohexylbenzene hydroperoxide, only a thin foam layer was observed even at a high flow rate of the air stream, as indicated by the relatively low foam layer height (curve 103) compared to curve 101. At a cyclohexylbenzene hydroperoxide concentration of 23 wt %, the foam layer height was essentially negligible.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

Non-limiting aspects and/or embodiments of the processes according to the present disclosure include:

E1. A process for oxidizing a first hydrocarbon, in certain embodiments to produce a first oxygenate, the process comprising:

(S-I) feeding a first feedstock comprising the first hydrocarbon into an oxidation reactor to obtain a reaction medium;

(S-II) contacting the reaction medium with a gas stream comprising $O_2$ in the oxidation reactor; and (S-III) supplying a hydroperoxide additive to the oxidation reactor such that the total concentration of hydroperoxide compound(s) in the reaction medium is in a range from 3.1 wt % to 20.0 wt %, based on the total weight of the reaction medium in the oxidation reactor.

E2. The process according to E1, wherein in step (S-II), the gas stream is passed through the reaction medium in the reactor, and in step (III), the hydroperoxide additive is supplied to the reactor such that the reaction medium has an average concentration of the hydroperoxide additive in the first three hours after the gas stream starts passing through the reaction medium of CHPXD(1), where 5.0 wt %≤CHPXD(1)≤20.0 wt %.

E3. The process according to E1 or E2, wherein the first hydrocarbon is an alkyl-substituted aromatic compound.

E4. The process according to any of E1 to E3, wherein the first oxygenate is a first hydroperoxide of the first hydrocarbon.

E5. The process according to any of E2 to E4, wherein CHPXD(1)≥6.0 wt %, in certain embodiments CHPXD(1)≥7.0 wt %, in certain embodiments CHPXD(1)≥8.0 wt %, in certain embodiments CHPXD(1)≥9.0 wt %, in certain embodiments CHPXD(1)≥10.0 wt %.

E6. The process according to any of E2 to E5, wherein CHPXD(1)≤8.0 wt %, in certain embodiments CHPXD(1)≤7.0 wt %, in certain embodiments CHPXD(1)≤6.0 wt %.

E7. The process according to any of E1 to E6, wherein the first oxygenate is a first hydroperoxide of the first hydrocarbon, and the first hydroperoxide and the hydroperoxide additive are the same.

E8. The process according to any of E1 to E7, wherein the hydroperoxide additive comprises at least one of cyclohexylbenzene hydroperoxide, sec-butylbenzene hydroperoxide, cumene hydroperoxide, cyclohexane hydroperoxide, and cyclohexylbenzene hydroperoxide.

E9. The process according to any of E1 to E8, wherein the first oxygenate and the hydroperoxide additive comprise cyclohexylbenzene hydroperoxide.

E10. The process according to any of E1 to E9, wherein the temperature of the reaction medium in step (S-II) is in a range from 70° C. to 130° C., in certain embodiments from 80° C. to 100° C., in certain other embodiments from 90° C. to 100° C.

E11. The process according to any of E1 to E10, wherein the absolute pressure inside the oxidation reactor in step (S-II) is in a range from 101 kPa to 2000 kPa, in certain embodiments from 101 kPa to 800 kPa, in certain embodiments from 101 kPa to 300 kPa.

E12. The process according to any of E1 to E11, wherein a foam layer forms atop the first feedstock at least at and/or close to the beginning of step (S-II), the foam layer having an average height HH1 in the first 24 hours of step (S-II), where HH1≤aa cm, where in various embodiments aa can be: 30; 25; 20; 15; 10; 8.0; 5.0; 3.0; 2.0; and even 1.0.

E13. The process according to any of E1 to E12, wherein a foam layer forms atop the first feedstock at least at and/or close to the beginning of step (S-II), the foam layer having an average height HH2 in the first three hours of step (S-II), where HH2≤aa cm, where in various embodiments aa can be: 30; 25; 20; 15; 10; 8.0; 5.0; 3.0; 2.0; and even 1.0.

E14. The process according to any of E1 to E13, wherein a foam layer forms atop the first feedstock at least at and/or close to the beginning of step (S-II), the foam layer having an average height HH3 in the first 72 hours of step (S-II), where HH3≤aa cm, where in various embodiments aa can be: 30; 25; 20; 15; 10; 8.0; 5.0; 3.0; 2.0; and even 1.0.

E15. The process according to any of E1 to E14, wherein in step (S-II) the flow rate of the gas stream is in a range from 5 to 100 $m^3 \cdot min^{-1}$, in certain embodiments from 10 to 80 $m^3 \cdot min^{-1}$, per kilogram of the reaction medium.

E16. The process according to any of E1 to E15, further comprising:

(S-IV) measuring a first pressure inside the oxidation reactor at a first location in proximity to and above a projected level of the top surface of the first feedstock using a first pressure sensor; and (S-V) measuring a second pressure inside the oxidation reactor at a second location in proximity to and below the projected level of the top surface of the reaction medium using a second pressure sensor.

E17. The process according to any of E11 to E16, further comprising:

(S-VI) controlling at least one reaction condition parameter inside the oxidation reactor based on the first pressure measured in step (S-IV) and the second pressure measured in step (S-V).

E18. The process according to E17, wherein in step (S-VI) the controlling is further based on an average density of the first feedstock and gas stream passing through the first feedstock without a foam layer on the top surface of the first feedstock.

E19. The process according to any of E1 to E18, further comprising: (S-VII) stirring the reaction medium using a mechanical stirrer and/or a liquid jet.

E20. The process according to E19, wherein in step (S-VII) the liquid jet is used, and the liquid jet comprises a portion of the first feedstock.

E21. The process according to E19, wherein in step (S-BIII) the liquid jet is used and the liquid jet comprises a portion of the reaction medium obtained from and recirculated back into the oxidation reactor.

E22. The process according to any of E1 to E21, further comprising a step (S-VIII) as follows:

(S-VIII) maintaining a substantially steady concentration of the first oxygenate in the oxidation reactor.

E23. The process according to E22, wherein in step (S-VIII) the substantially steady concentration of the first oxygenate is at most 25 wt %, or at most 20 wt %, or at most 15 wt %, or at most 10 wt %.

E24. The process according to E23, wherein in step (S-VIII) the substantially steady concentration of the first oxygenate is at least 4.0 wt %, or at least 5.0 wt %, or at least 8.0 wt %, or at least 10 wt %.

E25. The process according to any of E1 to E24, wherein the reaction medium further comprises a cyclic imide of the general formula (F-III), described above, in certain embodiments a cyclic imide of the general formula (F-IV), described above, and in certain embodiments NHPI.

E26. The process according to any of E1 to E25, wherein the oxidation reactor is a continuous reactor, the period of time required to achieve a steady concentration of the first oxygenate in the reactor is P1, and $0.10 \leq P1/P2 \leq 0.95$, where P2 is the period of time required to achieve a steady concentration of the first oxygenate in the reactor in an otherwise identical process except that no hydroperoxide additive is supplied to the reaction medium.

E27. The process for making cyclohexanone and/or phenol, comprising the following steps:

(S-A) contacting benzene and $H_2$ with a hydroalkylation catalyst under a hydroalkylation condition effective to produce a hydroalkylation effluent comprising cyclohexylbenzene;

(S-B) oxidizing at least a portion of the cyclohexylbenzene in the hydroalkylation effluent in an oxidation reactor to produce an oxidation reaction effluent comprising cyclohexylbenzene hydroperoxide by:

(S-BI) feeding a first feedstock comprising the at least a portion of the cyclohexylbenzene into the oxidation reactor to obtain a reaction medium;

(S-BII) contacting the reaction medium with a gas stream comprising $O_2$ in the oxidation reactor; and (S-BIII) supplying a hydroperoxide additive to the oxidation reactor such that the total concentration of hydroperoxide compound(s) is in a range from 0.5 wt % to 20.0 wt %, based on the total weight of the reaction medium in the oxidation reactor; and (S-C) subjecting at least a portion of the cyclohexylbenzene hydroperoxide in the oxidation reaction effluent to a cleavage reaction to obtain a cleavage effluent comprising cyclohexanone and phenol.

E28. The process according to E27, wherein in step (S-BII) the gas stream is passed through the reaction medium in the reactor, and in step (S-BII) the hydroperoxide additive is supplied to the reactor such that the reaction medium has an average concentration of the hydroperoxide additive in the first three hours after the $O_2$-containing gas stream starts passing through the reaction medium of CHPXD(1), where 0.5 wt % $\leq$ CHPXD(1) $\leq$ 20.0 wt %, in certain embodiments CHPXD(1) $\geq$ XX wt %, where XX in various embodiments is: 0.6; 0.8; 1.0; 1.5; 2.0; 2.5; 3.0; 3.5; 4.0; 4.5; or 5.0.

E29. The process according to E28, wherein CHPXD(1) $\leq$ YY wt %, where YY in certain embodiments is: 15.0; 12.0; 10.0; 8.0; 7.0; 6.0; 5.0; 4.0; or 3.0.

E30. The process according to any of E27 to E29, wherein the hydroperoxide additive is cyclohexylbenzene hydroperoxide.

E31. The process according to any of E27 to E30, wherein the hydroperoxide additive is selected from sec-butylbenzene hydroperoxide, cumene hydroperoxide, and cyclohexane hydroperoxide.

E32. The process according to any of E27 to E31, wherein the temperature of the reaction medium in step (S-BII) is in a range from 80° C. to 130° C., in certain embodiments from 90° C. to 120° C., in certain other embodiments from 100° C. to 110° C.

E33. The process according to any of E27 to E32, wherein the absolute pressure inside the oxidation reactor in step (S-BII) is in a range from 101 kPa to 2000 kPa, in certain embodiments from 101 kPa to 1000 kPa.

E34. The process according to any of E27 to E33, wherein a foam layer forms atop the reaction medium at least at and/or close to the beginning of step (S-BII), the foam layer having an average height HH1 in the first 24 hours of step (S-BII), where HH1 $\leq$ aa cm, where in various embodiments aa can be: 30; 25; 20; 15; 10; 8.0; 5.0; 3.0; 2.0; and even 1.0.

E35. The process according to any of E27 to E34, wherein a foam layer forms atop the reaction medium at least at and/or close to the beginning of step (S-BII), the foam layer having an average height HH2 in the first three hours of step (S-BII), where HH2 $\leq$ aa cm, where in various embodiments aa can be: 30; 25; 20; 15; 10; 8.0; 5.0; 3.0; 2.0; and even 1.0.

E36. The process according to any of E27 to E35, wherein a foam layer forms atop the reaction medium at least at and/or close to the beginning of step (S-BII), the foam layer having an average height HH3 in the first 72 hours of step (S-BII), where HH3 $\leq$ aa cm, where in various embodiments aa can be: 30; 25; 20; 15; 10; 8.0; 5.0; 3.0; 2.0; and even 1.0.

E37. The process according to any of E27 to E36, wherein in step (S-BII), the flow rate of the gas stream is in a range from 5 to 100 $m^3 \cdot min^{-1}$, in certain embodiments from 10 to 80 $m^3 \cdot min^{-1}$, per kilogram of the reaction medium.

E38. The process according to any of E27 to E37, wherein step (S-B) further comprises:

(S-BIV) measuring a first pressure inside the oxidation reactor at a first location in proximity to and above a projected level of the top surface of the reaction medium using a first pressure sensor; and (S-BV) measuring a second pressure inside the oxidation reactor at a second location in proximity to and below the projected level of the top surface of the reaction medium using a second pressure sensor.

E39. The process according to E38, wherein step (S-B) further comprises:

(S-BVI) controlling at least one reaction condition parameter inside the oxidation reactor based on the first pressure measured in step (S-BIV) and the second pressure measured in step (S-BV).

E40. The process according to E39, wherein in step (S-BVI) the controlling is further based on an average density of the reaction medium and the gas stream passing through the reaction medium without a foam layer on the top surface of the reaction medium.

E41. The process according to any of E27 to E40, wherein step (S-B) further comprises:

(S-BVII) stirring the reaction medium using a mechanical stirrer and/or a liquid jet.

E42. The process according to E41, wherein in step (S-BVII) the liquid jet is used, and the liquid jet comprises a portion of the first feedstock.

E43. The process according to E41, wherein the liquid jet is used and the liquid jet comprises a portion of the reaction medium obtained from and recirculated back into the oxidation reactor.

E44. The process according to any of E27 to E43, wherein the reaction medium further comprises a cyclic imide of the general formula (F-III), described above, and in certain embodiments, a cyclic imide of the general formula (F-IV), described above, and in certain embodiments, NHPI.

E45. The process according to any of E27 to E44, wherein the oxidation reactor is a continuous reactor, the period of time required to achieve a steady concentration of the first oxygenate in the reactor is P1, and $0.10 \leq P1/P2 \leq 0.95$, where P2 is the period of time required to achieve a steady concentration of the first oxygenate in the reactor in an otherwise identical process except that no hydroperoxide additive is supplied to the reaction medium.

The invention claimed is:

1. A process for oxidizing a first hydrocarbon, the process comprising:
   (S-I) feeding a first feedstock comprising the first hydrocarbon into an oxidation reactor to obtain a reaction medium;
   (S-II) contacting the reaction medium with a gas stream comprising $O_2$ in the oxidation reactor;
   (S-III) supplying a hydroperoxide additive to the oxidation reactor such that the total concentration of hydroperoxide compound(s) in the reaction medium is in a range from 3.1 wt % to 20.0 wt %, based on the total weight of the reaction medium in the oxidation reactor;
   (S-IV) measuring a first pressure inside the oxidation reactor at a first location in proximity to and above a projected level of the top surface of the reaction medium;
   (S-V) measuring a second pressure inside the oxidation reactor at a second location in proximity to and below the projected level of the top surface of the reaction medium; and
   (S-VI) controlling at least one reaction condition parameter inside the oxidation reactor based on the first pressure measured in step (S-IV) and the second pressure measured in step (S-V).

2. The process according to claim 1, wherein the hydroperoxide additive of step (S-III) comprises a hydroperoxide of the first hydrocarbon.

3. The process according to claim 1, wherein the hydroperoxide additive in step (S-III) comprises at least one of cyclohexylbenzene hydroperoxide, sec-butylbenzene hydroperoxide, cumene hydroperoxide, and cyclohexane hydroperoxide.

4. The process according to claim 1, wherein the gas stream comprising $O_2$ is passed through the reaction medium in the oxidation reactor, and step (S-III) is carried out before or within two hours after the gas stream started passing through the reaction medium.

5. The process according to claim 1, wherein the contacting step (S-II) is conducted at a temperature of the reaction medium in a range from 70° C. to 130° C. and/or an absolute pressure inside the oxidation reactor in a range from 101 kPa to 800 kPa.

6. The process according to claim 1, wherein a foam layer forms atop the reaction medium at least at and/or close to the beginning of step (S-II), the foam layer having an average height HH1 in the first 24 hours of step (S-II), where HH1≤30 cm.

7. The process according to claim 1, wherein a foam layer forms atop the reaction medium at least at and/or close to the beginning of the contacting step (S-II), the foam layer having an average height HH2 in the first three hours of step (S-II), where HH2<30 cm.

8. The process according to claim 1, wherein in step (S-II), the flow rate of the gas stream is in a range from 5 to 100 $m^3 \cdot min^{-1}$ per kilogram of the reaction medium inside the oxidation reactor.

9. The process according to claim 1, wherein the oxidation reactor is a continuous reactor, a first oxygenate is produced from the oxidation of the first hydrocarbon, the period of time required to achieve a steady concentration of the first oxygenate in the oxidation reactor is P1, and $0.10 \le P1/P2 \le 0.95$, where P2 is the period of time required to achieve a steady concentration of the first oxygenate in the oxidation reactor in an otherwise identical process except that no hydroperoxide additive is supplied to the reaction medium.

10. The process according to claim 1, further comprising:
    (S-VII) stirring the reaction medium using a mechanical stirrer and/or a liquid jet.

11. The process according to claim 9, further comprising:
    (S-VIII) maintaining a substantially steady concentration of the first oxygenate in the oxidation reactor.

12. The process according to claim 1, wherein the reaction medium further comprises a cyclic imide of the general formula (F-III):

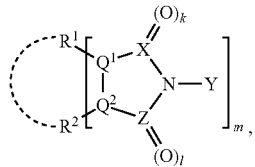

(F-III)

wherein each of $R^1$ and $R^2$, the same or different, is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I, or $R^1$ and $R^2$ can be linked to one another via a covalent bond to form a cyclic moiety with $Q^1$ and $Q^2$, defined below;
each of $Q^1$ and $Q^2$, the same or different, is independently selected from C, CH and $CR^3$, where $R^3$ is selected from hydrocarbyl and substituted hydrocarbyl radicals having 1 to 20 carbon atoms, $SO_3H$, $NH_2$, OH, $NO_2$, H, F, Cl, Br and I;
each of X and Z is independently selected from C, S, $CH_2$, N, P and elements of Group 4 of the Periodic Table;
Y is 0 or OH;
k is 0, 1 or 2;
l is 0, 1 or 2; and
m is 1, 2 or 3.

13. A process for making cyclohexanone and/or phenol, comprising the following steps:
    (S-A) contacting benzene and $H_2$ with a hydroalkylation catalyst under a hydroalkylation condition effective to produce a hydroalkylation effluent comprising cyclohexylbenzene;
    (S-B) oxidizing at least a portion of the cyclohexylbenzene in the hydroalkylation effluent in an oxidation reactor to produce an oxidation reaction effluent comprising cyclohexylbenzene hydroperoxide by:
    (S-BI) feeding a first feedstock comprising the at least a portion of the cyclohexylbenzene into the oxidation reactor to obtain a reaction medium;
    (S-BII) contacting the reaction medium with a gas stream comprising $O_2$ in the oxidation reactor;
    (S-BIII) supplying a hydroperoxide additive to the oxidation reactor such that the total concentration of hydroperoxide compound(s) is in a range from 0.5 wt % to 20.0 wt %, based on the total weight of the reaction medium in the oxidation reactor;
    (S-BIV) measuring a first pressure inside the oxidation reactor at a first location in proximity to and above a projected level of the top surface of the reaction medium;
    (S-BV) measuring a second pressure inside the oxidation reactor at a second location in proximity to and below the projected level of the top surface of reaction medium; and (S-BVI) controlling at least one reaction condition parameter inside the oxidation reactor based on the first pressure measured in step (S-BIV) and the second pressure measured in step (S-BV); and (S-C) subjecting at least a portion of the cyclohexylbenzene hydroperoxide in the oxidation reaction effluent to a cleavage reaction to obtain a cleavage effluent comprising cyclohexanone and phenol.

14. The process according to claim 13, wherein the hydroperoxide additive in step (S-BIII) comprises at least one of cyclohexylbenzene hydroperoxide, sec-butylbenzene hydroperoxide, cumene hydroperoxide and cyclohexane hydroperoxide.

15. The process according to claim 13, wherein the gas stream comprising $O_2$ is passed through the reaction medium in the oxidation reactor, and step (S-BIII) has been carried out before or within two hours after the gas stream started passing through the reaction medium.

16. The process according to claim 13, wherein the contacting step (S-BII) is conducted at a temperature of the reaction medium in the oxidation reactor in a range from 80° C. to 130° C. and/or an absolute pressure inside the oxidation reactor in a range from 101 kPa to 800 kPa.

17. The process according to claim 13, wherein a foam layer forms atop the reaction medium in the oxidation reactor at least at and/or close to the beginning of step (S-BII), the foam layer having an average height HH1 in the first 24 hours of step (S-BII), where HH1<30 cm.

18. The process according to claim 13, wherein a foam layer forms atop the reaction medium in the oxidation reactor at least at and/or close to the beginning of step (S-BII), the foam layer having an average height HH2 in the first three hours of step (S-BII), where HH2<30 cm.

19. The process according to claim 13, wherein step (S-B) further comprises:

(S-BVII) stirring the reaction medium using a mechanical stirrer and/or a liquid jet.

20. The process according to claim 13, wherein the oxidation reactor is a continuous reactor, the period of time required to achieve a steady concentration of cyclohexylbenzene hydroperoxide in the oxidation reactor is P1, and $0.10 \leq P1/P2 \leq 0.95$, where P2 is the period of time required to achieve a steady concentration of the cyclohexylbenzene hydroperoxide in the oxidation reactor in an otherwise identical process except that no hydroperoxide additive is supplied to the reaction medium.

21. The process according to claim 13, wherein step (S-B) further comprises:

(S-BVIII) maintaining a substantially steady concentration of the cyclohexylbenzene hydroperoxide in the oxidation reactor.

22. The process according to claim 13, wherein the reaction medium further comprises a cyclic imide of the general formula (F-III):

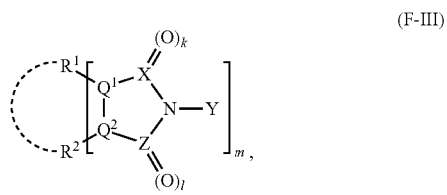

(F-III)

wherein each of $R^1$ and $R^2$, the same or different, is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I, or $R^1$ and $R^2$ can be linked to one another via a covalent bond to form a cyclic moiety with $Q^1$ and $Q^2$, defined below;

each of $Q^1$ and $Q^2$, the same or different, is independently selected from C, CH and $CR^3$, where $R^3$ is selected from hydrocarbyl and substituted hydrocarbyl radicals having 1 to 20 carbon atoms, $SO_3H$, $NH_2$, OH, $NO_2$, H, F, Cl, Br and I;

each of X and Z is independently selected from C, S, $CH_2$, N, P and elements of Group 4 of the Periodic Table;

Y is 0 or OH;

k is 0, 1 or 2;

l is 0, 1 or 2; and m is 1, 2 or 3.

* * * * *